(12) United States Patent
Klemm

(10) Patent No.: US 11,654,247 B2
(45) Date of Patent: May 23, 2023

(54) CONTAINER FOR AN INJECTABLE MEDICAMENT

(71) Applicant: SANOFI, Paris (FR)

(72) Inventor: Thomas Klemm, Frankfurt am Main (DE)

(73) Assignee: Sanofi, Paris (FR)

( * ) Notice: Subject to any disclaimer, the term of this patent is extended or adjusted under 35 U.S.C. 154(b) by 348 days.

(21) Appl. No.: 16/964,701

(22) PCT Filed: Jan. 23, 2019

(86) PCT No.: PCT/EP2019/051551
§ 371 (c)(1),
(2) Date: Jul. 24, 2020

(87) PCT Pub. No.: WO2019/145317
PCT Pub. Date: Aug. 1, 2019

(65) Prior Publication Data
US 2021/0052814 A1  Feb. 25, 2021

(30) Foreign Application Priority Data

Jan. 26, 2018 (EP) ..................... 18305065

(51) Int. Cl.
*A61M 5/315* (2006.01)

(52) U.S. Cl.
CPC ...... *A61M 5/3157* (2013.01); *A61M 5/31513* (2013.01); *A61M 2205/3375* (2013.01); *A61M 2205/3576* (2013.01); *A61M 2205/50* (2013.01)

(58) Field of Classification Search
CPC ......... A61M 5/3157; A61M 2205/3379; G01F 17/00; G01S 15/02; G01H 13/00; F15B 15/2869–2884
See application file for complete search history.

(56) References Cited

U.S. PATENT DOCUMENTS 10,245,378 B2 * 4/2019 Raman ............ A61M 5/14224
2015/0174330 A1 6/2015 Nagel et al.
(Continued)

FOREIGN PATENT DOCUMENTS

JP 2015-529481 10/2015
WO WO 2014/009442 1/2014
(Continued)

OTHER PUBLICATIONS

PCT International Preliminary Report on Patentability in International Appln. No. PCT/EP2019/051551, dated Jul. 28, 2020, 7 pages.
(Continued)

*Primary Examiner* — Bhisma Mehta
*Assistant Examiner* — John J Crawford
(74) *Attorney, Agent, or Firm* — Fish & Richardson P.C.

(57) ABSTRACT

A container for an injectable medicament is provided. The container can include an elongated body having a tubular-shaped sidewall extending along a longitudinal axis and having a distal end and a proximal end. The container can include an outlet at the distal end and a bung arranged inside the elongated body, sealingly engaged with the sidewall and slidable along the longitudinal axis relative to the sidewall. The container can include an interior volume to receive the injectable medicament and being confined by the sidewall, the outlet, and the bung. The container can include a measuring arrangement arranged in or on the bung. The measuring arrangement can include a signal generator configured to emit a measurement signal into or through the interior volume, the measurement signal being capable to stimulate or to excite a resonance of the container. The measuring arrangement can include a signal detector configured to detect a feedback signal indicative of a resonating (Continued)

interaction of the measurement signal with at least one of the sidewall, the outlet or the interior volume.

22 Claims, 3 Drawing Sheets

(56) References Cited

U.S. PATENT DOCUMENTS

| | | | |
|---|---|---|---|
| 2015/0174342 A1 | 6/2015 | Mitrosky et al. | |
| 2017/0182251 A1* | 6/2017 | Nagel | A61M 5/1684 |
| 2017/0312430 A1 | 11/2017 | Schleicher | |
| 2017/0312455 A1* | 11/2017 | Mirov | A61M 5/31568 |
| 2017/0316177 A1 | 11/2017 | Mirov et al. | |
| 2019/0054252 A1* | 2/2019 | Amschler | A61M 5/24 |

FOREIGN PATENT DOCUMENTS

| | | |
|---|---|---|
| WO | WO 2015/109251 | 7/2015 |
| WO | WO 2016/140853 | 9/2016 |
| WO | WO 2017/155672 | 9/2017 |

OTHER PUBLICATIONS

PCT International Search Report and Written opinion in International Appln. No. PCT/EP2019/051551, dated Apr. 3, 2019, 10 pages.

\* cited by examiner

CONTAINER FOR AN INJECTABLE MEDICAMENT

CROSS REFERENCE TO RELATED APPLICATIONS

The present application is the national stage entry of International Patent Application No. PCT/EP2019/051551, filed on Jan. 23, 2019, and claims priority to Application No. EP 18305065.7, filed on Jan. 26, 2018, the disclosures of each of which are incorporated herein by reference.

TECHNICAL FIELD

The present disclosure relates to measuring an interior volume of a container filled with a liquid substance, typically filled with an injectable medicament. The disclosure relates to a container for an injectable medicament. The container allows and supports a precise measurement of the size of an interior volume of the container occupied by the injectable medicament. The disclosure also relates to a method of determining the size of an interior volume of such a container.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod to operably engage with a bung or piston of the cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a filled one. In contrast to that, drug delivery devices of disposable type are to be entirely discarded when the medicament in the cartridge has been dispensed or used-up.

It is desirable to determine the amount of the medicament remaining in a cartridge while the cartridge is arranged inside a drug delivery device. It is a further aim to determine an interior volume of the cartridge occupied by the liquid injectable medicament. Determination of measurement of the interior volume should be rather precise, reliable and highly reproducible. It is desirable to provide a container for injectable medicament readily equipped with volumetric measurement means that enables and supports electronic data processing.

SUMMARY

This disclosure provides a container for an injectable medicament. The container comprises an elongated body having a tubular-shaped sidewall extending along a longitudinal axis (z) and having a distal end and a proximal end. The distal end is located opposite to the proximal end. The container further comprises an outlet at the distal end of the elongated body. The container further comprises a bung or a piston arranged inside the elongated body. The bung is sealingly engaged with the sidewall and is slidable along the longitudinal axis relative to the sidewall. The container further comprises an interior volume that may be also denoted as a filling volume. The interior volume or filling volume is configured to receive and to contain the injectable medicament. The interior volume is confined by the sidewall, by the outlet and by the bung.

The container further comprises a measuring arrangement that is arranged in or on the bung. The measuring arrangement comprises a signal generator that is configured to emit a measurement signal into or through the interior volume. The measurement signal is capable to stimulate or to excite a resonance of the container or a component thereof. The measurement signal is particularly capable to stimulate or to excite an acoustic resonance of at least one of the container as such or to stimulate or to excite an acoustic resonance of at least one of the elongated body, the outlet and the bung of the container.

The measuring arrangement further comprises a signal detector configured to detect a feedback signal that is indicative of a resonating interaction of the measurement signal with at least one of the sidewall, the outlet or the interior volume. The feedback signal may be indicative of a resonating interaction of the measurement signal with at least one of the container, the interior volume of the container or the injectable medicament located inside the interior volume. If the container and hence the interior volume is occupied or at least partially filled with the injectable medicament the feedback signal may be further indicative of an interaction of the measurement signal with the liquid medicament contained in the interior volume.

With the measuring arrangement in or on the bung a container with an integrated measuring arrangement is provided. The bung of the container may be readily equipped with the measuring arrangement. The signal generator and the signal detector of the measuring arrangement are configured to conduct a measurement by emitting measurement signals and by detecting feedback signals in return. The measurement signal and its interaction with at least one of the sidewall, the outlet, the interior volume or the injectable medicament leads to the generation of a detectable feedback signal. The detection of the feedback signal allows deriving of at least one physical or chemical parameter of the container. In particular, the feedback signal obtainable and detectable by the signal detector is processable to determine at least one of the size of the interior volume and the longitudinal position of the bung relative to the sidewall of the body of the container.

In a further example the signal detector is configured to detect a feedback signal that emanates from the signal generator during emission of the measurement signal. Insofar, the signal detector may be connected or coupled to the signal generator in order to monitor the emission of measurement signals conducted by the signal generator. From the emission behavior or from the emission of the signals produced, generated and emitted by the signal generator the signal detector may derive a feedback signal being indicative of a resonating interaction between the measurement signal with at least one of the sidewall, the outlet or the interior volume.

The integration of the signal generator and the signal detector into or on the bung makes a separate attachment and arrangement of signal generator and signal detector to the container superfluous. In order to provide a volumetric measurement of the interior or inside volume of the container it may be sufficient to provide the container with a particular bung as described above being equipped at least with a signal generator and a signal detector.

At least one of the signal generator and the signal detector or both, the signal generator and the signal detector may be located entirely inside the volume or inside the bulk of the bung. The signal generator and/or the signal detector may be entirely enclosed by the bung. With other examples at least one of the signal generator and the signal detector may be arranged at least partially inside the bung. A portion of at least one of the signal generator and the signal detector may flush with an outside surface of the bung. With other examples at least a portion of at least one of the signal generator and the signal detector may protrude from an outside surface of the bung, e.g. from a distal face of the bung. Since the signal generator is configured to emit a measurement signal into or through the interior volume the signal generator may be located near a distal face of the bung pointing towards the distally located outlet of the container. Also, the signal detector may be located at or close to the distal face of the bung so as to have immediate access to the interior volume.

With examples wherein at least one of the signal generator and the signal detector is entirely enclosed or embedded inside the bung either the measurement signal or the feedback signal may be configured to propagate through the bung. If the signal generator is located inside the bung at a non-zero distance from both, a distal end face and a proximal end face of the bung the measurement signal generated by the signal generator propagates through the bung and into the interior volume confined by the bung. If the signal detector is entirely embedded inside the bung at a non-zero distance from both, the distal end face and the proximal end face of the bung the feedback signal may also propagate from the interior volume into the bung in order to become detected by the signal detector.

By having the signal generator and the signal detector attached to or entirely located inside the bung even existing containers, such as cartridges for injectable medicaments and their elongated bodies can be retrofitted with a measuring arrangement. Here, an existing bung, typically configured as a rubber stopper can be exchanged by a bung as described above, which bung is equipped with the measuring arrangement.

Typically, the bung comprises an elastomeric material, such as natural or synthetic rubber. The bung may comprise a cyclic olefin polymer (COP) and/or a cyclic olefin copolymer. The bung may also comprise a polymer material on the basis of EPDM ethylene propylene diene monomer rubber. The measuring arrangement may be encapsulated inside the bung. The measuring arrangement may comprise a hermetic housing configured to accommodate at least the signal generator and the signal detector. The housing may be embedded inside the bulk of the bung.

For the encapsulation of at least one of the signal generator and the signal detector inside the housing of the measuring arrangement enables a multitude of different ways to manufacture the bung. For example, the housing with the signal generator and the signal detector located therein may be subject to an over-molding by a bung-forming material.

With other examples the bung may comprise at least two bung components that are configured to become mechanically assembled together to form the bung. Here, the measuring arrangement can be arranged between these bung components in order to embed the measuring arrangement inside the bung.

By embedding the measuring arrangement inside the bung the measuring arrangement is inherently protected against environmental influences or hazards. Moreover, the measuring arrangement can be concealed by and inside the bung. The embedding of the measuring arrangement inside the bung may have no influence on the outside geometry of the bung. If the measuring arrangement is entirely embedded inside the bung and hence enclosed by the bung it is not visible from outside. In this way, the measuring capability of the container can be effectively concealed. This may enable a concealed supervision or monitoring of the filling level of the container.

According to a further example the container comprises a processor connected to the signal detector. The processor may be arranged inside the bung. The processor may belong to the measuring arrangement. Hence, the measuring arrangement may comprise the processor. The processor is configured to process signals obtainable from the signal detector when receiving at least one feedback signal. The signal detector is typically configured to generate an electrical signal in response to receive a feedback signal. An electrically conductive connection between the processor and the signal detector enables a respective signal processing. Based on the signals obtainable from the signal detector the processor is configured to determine at least one of a size of the interior volume or the longitudinal position of the bung relative to the body of the container.

The processor may comprise an integrated circuit, such as an application specific integrated circuit (ASIC). The processor may be implemented as a microcontroller. The processor is at least electrically connected to the signal detector. The processor may be also located inside the bung. Typically, the processor is located on a printed circuit board (PCB). At least one of the signal generator and the signal detector may be located and integrated on the same PCB. The entire measuring arrangement may be configured or implemented as an ASIC and may be provided on a single common PCB. With other examples the processor may be located outside the measuring arrangement. The processor may be located on a proximal surface of the bung. It may be also located outside the bung or at a predefined non-zero distance from the bung.

The processor may be located even outside the container. The connection between the processor and the signal detector may be of wired or wireless type. When the processor is located inside or on the bung there is provided a wired connection between the processor and the signal detector. With examples wherein the processor is located outside the bung and/or outside the container the processor may be connected to the signal detector in a wireless way.

In a further example the processor is configured to determine a size of the interior volume on the basis of the feedback signal obtainable through the signal detector. For this, the processor may be configured to determine a magnitude or amplitude of the feedback signal. The processor may be configured to determine a time or time delay at which the feedback signal is detected compared to a reference signal. Alternatively, the processor may be configured to determine a phase shift between a feedback signal and a reference signal. The processor may be further configured to compare a feedback signal with a predefined signal or with a previously detected feedback signal. In this way, the processor may be configured to monitor and to process a temporal variation of the feedback signal or of a series of feedback signals. A temporary variation of the feedback signal may be indicative of the size of the interior volume and/or of the longitudinal position of the bung.

With a further example the processor is connected to the signal generator. Typically, the processor is connected to both, the signal generator and to the signal detector. Here, the processor is configured to trigger the emission of the measurement signal. The processor is further configured to determine the size of the interior volume on the basis of a comparison of at least one measurement signal with at least one feedback signal. The processor may be further configured to conduct a comparison of at least one measurement signal with several feedback signals. Alternatively or additionally the processor may be configured to compare at least one feedback signal with several measurement signals. Moreover, the processor may be configured to compare a multitude of measurement signals with a multitude of feedback signals.

The signal generator may be configured to emit a series or a sequence of measurement signals. Accordingly, the signal detector may be configured to detect a respective series or sequence of measurement signals in return. Here, the processor may be configured to conduct a mutual comparison of feedback signals of a sequence of feedback signals. In this way, temporal fluctuations of the feedback signal or of the feedback signals can be detected. Such a temporal fluctuation may be indicative of the size of the interior volume and/or of the longitudinal position of the bung relative to the body of the container.

Moreover, since the processor is connected to both, the signal generator and to the signal detector the processor may be configured to measure a time delay between the emission of a measurement signal by the signal generator and the detection of a feedback signal by the signal detector. From a determination of such a time delay the size of the interior volume and/or the longitudinal position of the bung may be precisely determined. In addition or as an alternative, the processor may be configured to compare the magnitude or amplitude of the feedback signal with a given reference amplitude. The amplitude or magnitude of the measurement signal may be directly indicative of the size of the interior volume and/or of the longitudinal position of the bung relative to the body.

In another example the measuring arrangement comprises a data storage configured to store at least one of an initial size of the interior volume and at least one feedback signal. The data storage may be configured to store an initial size of the interior volume or at least one feedback signal during a calibration procedure of the container. It is conceivable, that upon or after filling the container with the injectable medicament the measuring arrangement is triggered to conduct a measurement, i.e. to emit a measurement signal and to detect a feedback signal in return.

Such an initial measurement may enable a calibration of the container. In such an initial measurement procedure the interior volume derived by the processor and/or the feedback signal may be stored as a reference volume or as a reference signal in the data storage. For subsequent measurement procedures the volume derived or determined by the processor and/or the feedback signal obtainable through the signal detector may be compared to the reference volume and/or to the reference signal previously stored in the data storage. The processor may be configured to conduct a quantitative comparison between a feedback signal and the reference feedback signal previously stored in the data storage. From the size or magnitude of a feedback signal in comparison to the size or magnitude of the reference feedback signal the size of the interior volume and/or the longitudinal position of the bung may be derived directly.

The data storage is typically connected to the processor. It may be also connected to at least one of the signal generator and the signal detector. The connection between the processor and the data storage allows for comparing an actually detected feedback signal with a previously detected feedback signal. The data storage may comprise a buffer for a sequence of feedback signals. The signal detector may be configured to fill the buffer of the data storage as a sequence or series of feedback signals is detected by the signal detector. The buffer of the data storage and the sequence of feedback signals stored therein may become subject to a stepwise data processing. The data storage therefore enables a reduction of the demands to the processor in terms of computational power. The electric energy consumption of the processor and of the entire measuring arrangement may be decreased by making use of the data storage. The data storage is typically integrated into the integrated circuit of the measuring arrangement. It may be located on a common PCB of the measuring arrangement. The processor and the data storage may be located and arranged on a common PCB.

In a further example the container comprises a communication interface configured to exchange data with an external electronic device. The communication interface may be located inside the bung. It may belong to the measuring arrangement. Hence, the measuring arrangement may comprise the communication interface. The communication interface member located inside or outside a housing of the measuring arrangement. The communication interface may comprise a wireless communication interface. In a further example the communication interface is a wired communication interface. The communication interface is typically connected to the processor and/or to the data storage. The communication interface may be also directly or indirectly connected to at least one of the signal generator and the signal detector. The communication interface may be connected to both, the signal generator and to the signal detector. Typically, the communication interface is located inside the bung. The communication interface and the processor are connected through a wired connection.

In one example, the measuring arrangement may be located or encapsulated inside the bung while the communication interface is located on an outside surface of the bung, e.g. on the proximal face of the bung. The communication interface may be also integrated into the measuring arrangement. The communication interface may be located inside the housing of the measuring arrangement. The communication interface may be integrated into the integrated circuit of the measuring arrangement. The communication interface, the processor and the storage may be arranged on a common PCB.

The communication interface is configured to communicate with an external electronic device. The communication interface may be configured to communicate with the external electronic device in accordance to a well-defined communication standard or communication protocol, such as WIFI, Bluetooth, NFC or other radio frequency-based communication standards. The communication interface may be configured to exchange data with the external electronic device, such as data obtained and generated by the processor. The external electronic device may be a portable electronic device, such as a smartphone or a tablet computer.

The data exchange between the communication interface and the external electronic device may comprise unprocessed feedback signals detected by the signal detector and transmitted via the communication interface to the external electronic device. With such an example it is generally conceivable that it is the external electronic device that comprises a processor configured to process feedback signals detected by the signal detector and transmitted to the external electronic device via the communication interface. In this way, electric power consumption of the container and hence of the measuring arrangement may be reduced. Moreover, the processor can be provided outside and remote from the container. Manufacturing costs for the container and for the measuring arrangement integrated in the bung may be thus reduced.

According to a further example the container comprises an antenna configured to withdraw electric energy from a surrounding electromagnetic field. It may be the measuring arrangement that comprises the antenna. The antenna may be arranged in or on the bung of the container. Typically, the antenna is electrically connected to the processor. The antenna may be further directly electrically connected to the communication interface. The antenna may be integrated into the communication interface or vice versa, i.e. the communication interface may be integrated into the antenna. It is conceivable that the communication interface communicates with the external electronic device via the antenna.

The antenna may therefore provide a twofold functionality. It may enable data exchange with an external electronic device. Moreover, the antenna is configured to withdraw electric energy from a surrounding electromagnetic field. The antenna may therefore provide and supply the measuring arrangement with electrical energy obtainable from a surrounding electromagnetic field. The antenna may comprise a NFC antenna. The electric energy necessary to drive or to power the measuring arrangement may be exclusively provided by the antenna and may be exclusively withdrawn from a surrounding electromagnetic field. Alternatively or additionally the measuring arrangement may be equipped with an electric energy storage, such as a battery. In a further example the measuring arrangement and hence the bung may be connectable to an external source of electric energy. For instance, when assembled inside an injection device the bung may be brought in electrical contact with an electric energy source.

In a further example the measuring arrangement comprises an electric energy storage that is connected to the antenna. In this way, the antenna is configured to charge the electric energy storage. In situations where a surrounding electromagnetic field is absent the electric energy storage may provide sufficient electric energy to drive or to power the measuring arrangement. The electric energy storage is typically connected to the measuring arrangement. It is connected to the signal generator in order to generate and to emit a measurement signal.

The electric energy storage is also connected to the signal detector in order to enable detection of a feedback signal. The electric energy storage is connected to the processor in order to enable a processing of detected feedback signals. The electric energy storage may be further connected to the data storage. In this way, reading of data from the storage as well as writing data into the data storage becomes enabled. The electric energy storage is further connected to the communication interface so as to enable data exchange or data transmission to an external electronic device.

In another example the signal generator is an acoustic signal generator. The acoustic signal generator is configured to generate and to emit acoustic measurement signals of variable frequency. In particular, the acoustic signal generator is configured to generate and to emit acoustic measurement signals of a first frequency, of a second frequency, of a third frequency and so on, wherein the first, second and third frequencies distinguish from each other. The acoustic signal generator may be configured to generate discrete pulses of acoustic measurement signals. By means of temporally varying the frequency of the measurement signal or means of brining the frequency of a consecutive series of measurement signals, the resonating interaction between the measurement signal and the at least one of the sidewall, the outlet and the interior volume will be subject to respective changes. The resonant behavior typically depends on the frequency of the measurement signal emitted into the interior volume.

In a further example, the acoustic signal generator is configured to generate and to emit a sequence or a series of acoustic measurement signals of different frequency. Typically, the signal generator is configured to generate and to emit a series of measurement signals of increasing frequency or decreasing frequency. The signal generator may be configured to generate a series of measurement signal of a monotonically and/or constantly increasing or decreasing frequency.

The acoustic signal generator may be tunable with regard to the frequency of the acoustic measurement signal. Consecutive pulses of acoustic measurement signals may comprise different frequencies. Consecutive pulses of acoustic measurement signals may be frequency shifted with regard to each other. In particular, consecutive acoustic measurement signals may exhibit a constant frequency offset. Consecutive acoustic measurement signals, e.g. acoustic pulses may comprise an increasing or decreasing frequency shift.

The acoustic signal generator may be configured to emit a continuous acoustic measurement signal of variable frequency. In other words, the frequency of the acoustic measurement signal may be subject to regular or irregular variations. The frequency of the acoustic measurement signal may change continuously and/or monotonously. For instance, the frequency of the acoustic measurement signal may constantly and slowly increase from a minimum frequency to a maximum frequency. When the acoustic measurement signal is at the maximum frequency the acoustic signal generator may be configured to abruptly change the frequency of the acoustic measurement signal to the minimum frequency; or vice versa. Once the acoustic measurement signal reaches a maximum or minimum frequency it may return to the minimum or maximum frequency, respectively. Thereafter it may ramp up to the maximum frequency in a continuous way. For instance, the acoustic signal generator may be operable to conduct a frequency sweep. In the time domain the frequency of the acoustic measurement signal may exhibit a saw tooth profile or a triangular profile.

The acoustic signal generator may be configured to modify the frequency of the acoustic measurement signal. Alternatively, the acoustic signal generator may be driven by the processor and/or by the communication interface, wherein at least one of the processor and the communication interface provide a control signal that defines the frequency of the acoustic measurement signal. At least one of the acoustic signal generator, the processor and the communication interface may be further configured to modify the amplitude of the acoustic measurement signal.

The acoustic signal generator may comprise an electromechanical transducer. It may comprise a piezo crystal or a piezo ceramic component configured to convert an electric signal into a mechanical excitation state, e.g. a mechanical vibration. The acoustic signal generator may be operable in the audible spectral range. The acoustic signal generator may be operable in the ultrasound spectral range. When driven in the ultrasound range, the signals emitted by the acoustic signal generator are not audible to persons and/or animals. Insofar there is no perceivable interference between the acoustic signal generator and a person utilizing the container. When driven in the ultrasound spectral range the acoustic signal generator may be configured to generate and to emit acoustic measurement signals at a frequency above 20 kHz, at a frequency above 100 kHz, at a frequency above 1 MHz or at a frequency above 10 MHz.

When operated in the audible spectral range, i.e. when the mechanical transducer is configured to generate and to emit a measurement signal at a frequency of less than 20 kHz or less than 10 kHz, less than 5 kHz, less than 1 kHz, less than 500 kHz, less than 200 kHz, less than 100 kHz or less than 50 kHz mechanical resonance phenomena of the container may be stimulated or excited that might be easily and unequivocally detectable.

The acoustic signal generator may comprise a microelectromechanical (MEM) device. Implementation of the acoustic signal generator in a MEM device is rather space saving. Such devices can be easily implemented inside the bung of the container. They are further suitable for a mass manufacturing at moderate costs.

Since the acoustic signal generator is configured to emit acoustic measurement signals of variable frequency the acoustic signal generator can be used to stimulate or to excite an acoustic resonance of the container. The signal generator may be configured to excite or to stimulate a resonance frequency or a higher harmonic of the resonance frequency of the container. The resonance or eigenfrequency of the container and/or its higher harmonics is dependent at least on the total mass of the container. The resonance frequency and/or its higher harmonics is directly correlated to the amount of medicament located inside the interior volume of the container. As the injectable medicament is dispensed, i.e. expelled or withdrawn through the outlet the amount of medicament residing in the interior volume decreases. This has a direct influence on the resonance frequency. The acoustic signal generator and in particular the generation and emission of acoustic measurement signals of variable frequency enables a detection of a modification of the resonance frequency of the container and/or of its higher harmonics.

The relation between the resonance frequency and the size of the interior volume can be stored in a look up table and can be determined before the container is commercially distributed to end consumers. Such a lookup table can be stored inside the data storage. The relation between a filling volume or the size of the interior volume and the resonance frequency can be for instance individually measured during a filling procedure of the container. A previously measured relation or a calculation formula between the resonance frequency or higher harmonics and the size of the interior volume can be stored in the data storage of the measuring arrangement.

An excitation or stimulation of the container by an acoustic measurement signal having a frequency that matches with the resonance frequency of the container or with a higher harmonic thereof can be precisely detected by the signal detector and a respective feedback signal detected by the signal detector can be processes by the processor. Based on a look up table or based on a calibration the processor may be configured to assign a feedback signal, e.g. the frequency and/or amplitude of the feedback signal to a size of the interior volume.

According to another example the signal detector comprises an electric impedance measurement circuit connected to the acoustic signal generator. When implemented as an impedance measurement circuit the acoustic signal generator is typically driven or operated in a frequency sweep mode. The frequency of the acoustic measurement signal is subject to a continuous or stepwise modification. The variation of the frequency of the acoustic measurement signal follows a predefined schedule. The impedance measurement circuit monitors one of a voltage and a current present to the acoustic signal generator.

If the frequency of the acoustic measurement signal and hence the mechanical vibration of the acoustic signal generator matches with the resonance frequency of the container or a higher harmonic of the reference frequency the voltage across the acoustic signal generator or a current through the acoustic signal generator exhibits a positive or negative peak. Such a peak can be detected by the electric impedance measurement circuit and/or by the processor connected to the impedance measurement circuit. Since the sweep of the frequency of the acoustic measurement signal is typically driven by a clock signal there is an unambiguous assignment between the momentary frequency of the acoustic measurement signal and the clock signal. The impedance measurement circuit and/or the processor connected thereto may then be configured to determine at least one clock signal where the output of the impedance measurement circuit exhibits a maximum or a minimum. The frequency that matches with this particular clock signal then represents the resonance frequency or a higher harmonic of the container at that time.

In a further example the signal detector is integrated into the signal generator. Alternatively, the signals detector is a component of the signal generator. By integrating the signal detector into the signal generator a separate signal detector or signal receiver becomes superfluous. This enables a rather compact and low-cost design of the measuring arrangement. A rather compact measuring arrangement is of particular benefit for arranging or embedding the measuring arrangement inside the bung of the container.

In another example the signal detector comprises an acoustic sensor. The acoustic sensor comprises a transducer configured to convert acoustic signals into electrical signals. The acoustic sensor may comprise a microphone. The acoustic sensor may be configured to monitor and/or to detect the feedback signal(s) emanating from at least one of the sidewall, the outlet or the interior volume of the container. The acoustic sensor may be configured to determine and to detect or to measure at least one of a frequency and an amplitude of the feedback signal. When the container is excited or stimulated with a resonance frequency an acoustic feedback signal detectable by the acoustic sensor may exhibit a maximum amplitude at a particular frequency of the feedback signal. The frequency of the feedback signal may directly represent the resonance frequency.

According to another aspect the disclosure further relates to a method of determining the size of an interior volume of a container as described above. The method comprises the steps of generating and emitting a measurement signal from the measuring arrangement into or through the interior volume of the container. The measurement signal is capable to stimulate or to excite a resonance of the container. Thereafter, at least one feedback signal is detected, typically by the signal detector. The detected feedback signal is indicative of an interaction of the measurement signal with at least one of the sidewall, the outlet or the interior volume of the container. Thereafter and in a final step the size of the interior volume is determined on the basis of the feedback signal. Typically, the method is conducted by a processor located inside the bung or provided outside the bung. The processor may be integrated into the measuring arrangement. With other examples the processor may be located in an external electronic device. Here, the measuring arrangement may be equipped with a communication interface configured to transmit or to exchange data with the external electronic device. The communication interface is then connected to at least one of the signal generator and the signal detector. It may be connected to both, the signal generator and the signal detector.

Generally speaking, the method of determining the size of an interior volume of the container is conducted by means of the container as described above. Accordingly, any features, benefits and modes of operation described above in connection with the container equally apply to the method of determining the size of the interior volume of the container; and vice versa.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope thereof. Further, it is to be noted, that any reference numerals used in the appended claims are not to be construed as limiting the scope of the disclosure.

In the following, numerous examples of the container and of an injection device will be described in greater detail by making reference to the drawings, in which:

DETAILED DESCRIPTION

Figure 1:
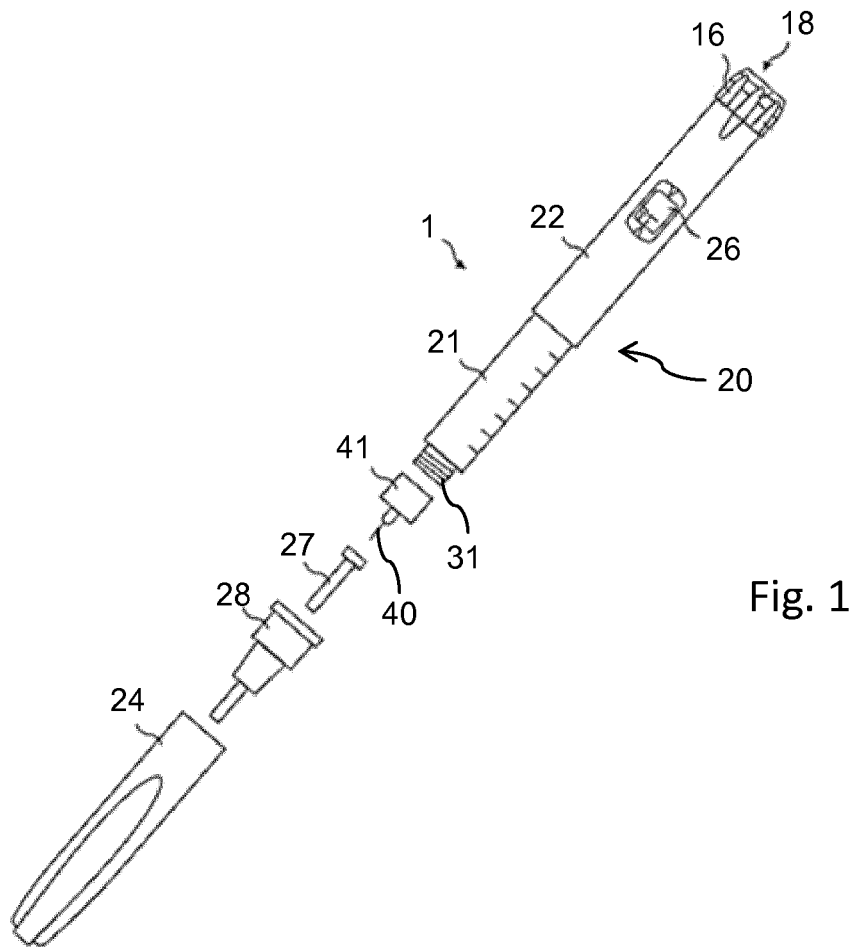
FIG. 1 shows an example of an injection device.
Figure 2:
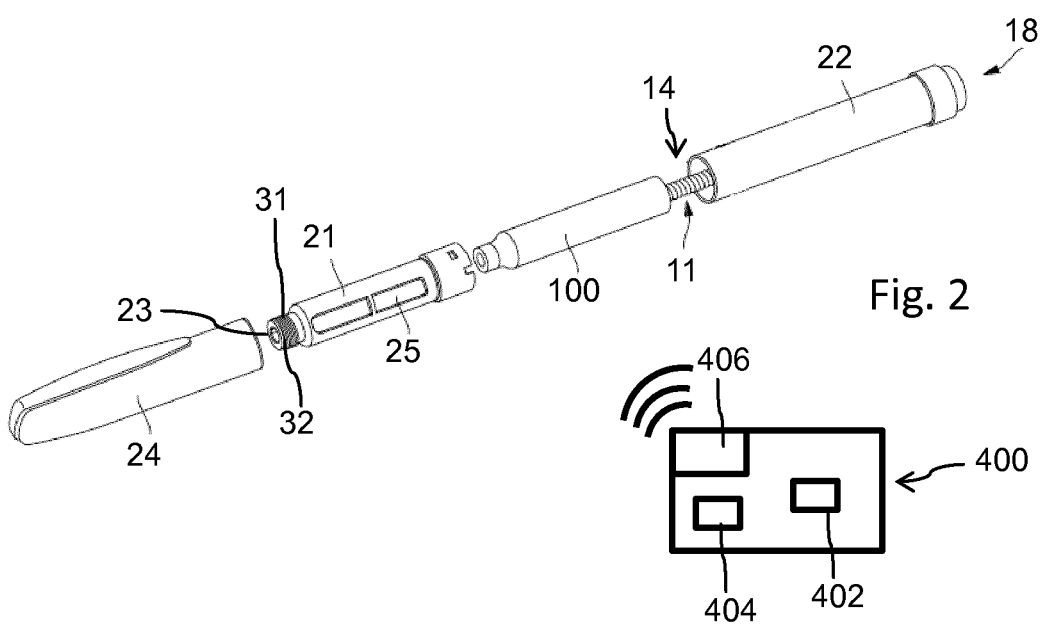
FIG. 2 shows the injection device partially disassembled and equipped with a container filled with an injectable medicament.

In FIGS. 1-2 an example of an injection device 1 configured as a pen type injector is illustrated. The injection device 1 comprises a housing 20. The housing 20 comprises a cartridge holder 21 and a body 22. The cartridge holder 21 is configured to accommodate a container 100 that may comprise a cartridge that is prefilled with at least a first injectable medicament 50. The cartridge holder 21 and the body 22 may be permanently or releasably attached to each other. With a permanent or non-releasable connection of cartridge holder 21 and body 22 the injection device 1 may be configured as a disposable injection device with the container 100 readily assembled therein. Alternatively, the injection device 1 may be configured as a reusable device.

Here, the cartridge holder 21 can be disconnected from the body 22 to replace or to exchange a container 100.

The cartridge holder 21 as illustrated in FIG. 2 comprises a window 25 to allow visual inspection of the container 100 located therein. Near a distal end the cartridge holder 21 comprises a socket 31 having an outer threaded section 32. The socket 31 is configured to support an injection needle 40. The injection needle 40 typically comprises a double-tipped hollow cannula having a proximal end and a distal end. The injection needle 40 typically comprises a needle hub 41 with an inside threaded portion for releasable connection with the threaded section 132. The needle hub 41 comprises a bottom section and a sidewall section forming a cup-shaped receptacle configured to receive the threaded socket 31 of the cartridge holder 21. The sidewall section comprises the inner threaded section that mates with the outer threaded section 32 of the socket 31. A distal end face of the cartridge holder 21 comprises a through opening 23 through which the proximally protruding portion of the needle 40 can extend into the interior of the cartridge holder 21 and hence into the interior of the cartridge or container 100 when the injection needle 40 is attached to the cartridge holder 21 and when the container 100 is arranged in the cartridge holder 21.

The container 100 is arranged inside the cartridge holder 21. It is positionally fixed inside the cartridge holder 21. The container 100 comprises an elongated and tubular-shaped body 101. The body 101 may comprise a vitreous body. The body 101 may be made of glass. The body 101 may be translucent or transparent in order to allow visual inspection of the content of the container 100. The elongated body 101 extends along a longitudinal direction (z). The body 101 comprises the distal end 103 and an oppositely located proximal end 104.

With the distal end 103 the body 101 is arranged near or at the distal end of the cartridge holder 21. The distal end 103 of the body 101 comprises a narrowing shoulder portion 107 extending into a diameter reduced neck portion 105. The radially narrowing shoulder portion 107 is configured to abut or to engage axially with a correspondingly-shaped shoulder section of the cartridge holder 21. The shoulder portion 107 is located close to the distal end 103 of the cartridge or container 100.

At the far distal end the neck portion 105 extends into a radially widening head portion 105a. At the head portion 105a there is provided a seal 106, e.g. in form of a pierceable sealing disc. This seal 106 may comprise a pierceable rubber septum that is fixed to the head portion 105a and hence to the distal end 103 of the body 101 by means of a ferrule 108 or crimped metal cap. The ferrule 108 may comprise a crimped aluminium cap. The seal 106 may form or belong to an outlet 109 of the container 100 at the distal end 103 of the elongated body 101.

The injection device 100 may be further equipped with a drive mechanism 14 comprising a plunger or a piston rod 11. The drive mechanism 14 may be further equipped with a trigger 18 by way of which a dispensing action of the injection device 1 can be triggered or controlled. Optionally, the injection device 1 and the drive mechanism 14 comprise a dose dial 16 by way of which a size of a dose to be dispensed can be individually set or by way of which the injection device 1 can be deployed or prepared for a subsequent dispensing procedure.

Optionally and as illustrated in FIG. 1 the body 22 of the housing 20 may be provided with a dose size indicating window 26. In the window 26 the size of a dose actually set can be visually displayed thus informing the user of the amount of the medicament to be dispensed during a subsequent dispensing procedure.

As further illustrated in FIG. 1 the injection needle 40 may be provided with an inner needle cap 27 configured to cover the distal end of the injection needle 40. The injection needle and/or the needle hub 41 may be further covered by an outer needle cap 28. If not in use the injection needle 40 should be detached from the distal end of the cartridge holder 21. Then, the cartridge holder 21 can and should be covered by a protective cap 24. The protective cap 124 is configured to releasably engage with at least one of the cartridge holder 21 and the body 22. Prior to assemble the injection needle 40 to the cartridge holder 21 the protective cap 24 has to be detached from the housing 20.

The above described interaction of the container 100 with a pen type injection device 1 as illustrated in FIGS. 1-2 is only exemplary. The general working principle of the container does not require interaction with a pen type injection device 1. Generally, the container 100 can be implemented or may be used as a manually operated syringe or as a container for an infusion device.

Figure 3:
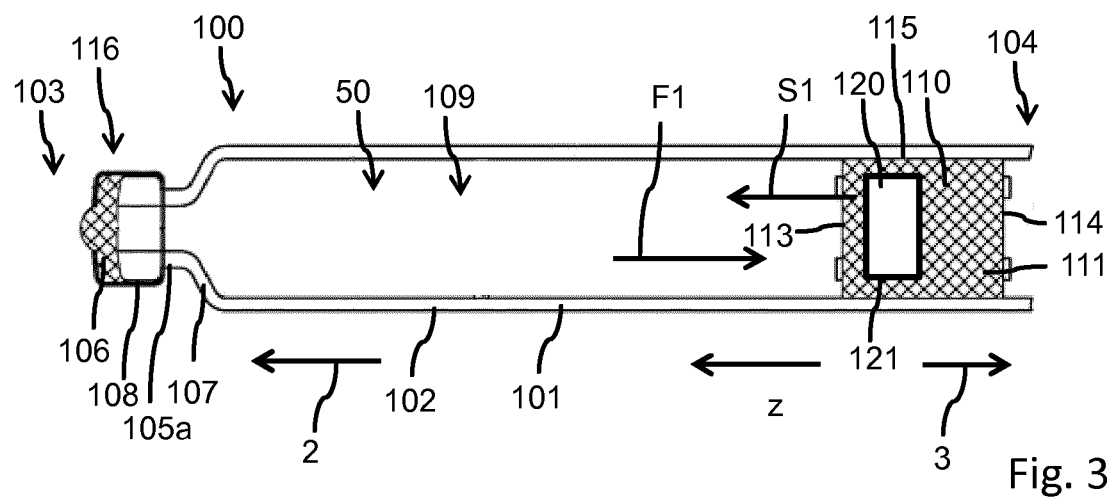
FIG. 3 shows a longitudinal cross-section through an example of the container.

The container 100 as illustrated in FIG. 3 comprises a tubular-shaped elongated body 101 having a tubular-shaped sidewall 102. At the distal end 103 the container 100 comprises an outlet 116. The outlet 116 is sealed by the pierceable seal 106. Near a proximal end 104 that is opposite to the distal end 103 the container 100 comprises a bung 110 or a piston. The bung 110 is arranged inside the tubular-shaped sidewall 101 of the container 100. The bung 110 is sealingly engaged with an inside section of the sidewall 102. The bung 110 comprises an outer tubular shaped sidewall 115 in frictional engagement with an inside of the sidewall 102 of the container 100.

The cross-section or diameter of the bung 110 matches with the respective cross-section or diameter of the body 101 and of its sidewall 102. The bung 110 comprises a body 111. The bung 110 comprises a distal face 113 facing towards the outlet 116 and hence towards the pierceable seal 106. Opposite to the distal face 113 the bung 110 comprises a proximal face 114. The proximal face 114 serves as a thrust receiving face of the bung 110. The proximal face 114 may get in axial or longitudinal abutment with the piston rod 11 of the drive mechanism 14 of an injection device 1 as illustrated in FIGS. 1 and 2.

In this way, the bung 110 can be urged or pushed in distal direction 2 so as to expel a predefined amount of the injectable medicament 50 from an interior volume 109 of the container 100. The interior volume 109 is confined in circumferential direction or in radial direction by the sidewall 102 of the container 100. In distal direction 2 the interior volume 109 is confined by the outlet 116. The interior volume 109 may be confined in distal direction 2 by the pierceable seal 106. In proximal direction 3 the interior volume 109 is confined by the bung 110. In particular, the interior volume 109 is confined by the distal face 113 of the bung 110.

The interior volume 109 defines the amount of injectable medicament 50 accommodated inside the container 100. During use of the container 100 and as the injectable medicament 50 is expelled from the interior of the container 100 the size of the interior volume 109 decreases as the bung 110 is driven in distal direction 2 towards the outlet 116. In order to measure or to determine the size of the interior volume 109 the bung 110 comprises a measuring arrangement 120. The measuring arrangement 120 is arranged in or on the bung 110. The measuring arrangement 120 may be encapsulated entirely inside a body 111 of the bung 110. The measuring arrangement 120 may be located inside the bung 110 at a predefined non-zero distance from any of the distal face 113, the proximal face 114 and the outer sidewall 115 of the bung.

In one example the measuring arrangement 120 comprises a housing 121. The measuring arrangement 120 or at least one component thereof may be alternatively arranged inside the bung 110 and outside the housing 121 so that the measuring arrangement 120 or at least one component thereof is arranged flush with an outer surface of the body 111 of the bung 110. For instance, the measuring arrangement 120 may flush with the distal face 113 or with the proximal face 114. The measuring arrangement 120 or components thereof may also protrude from at least one of the distal face 113 and the proximal face 114.

Figure 4:
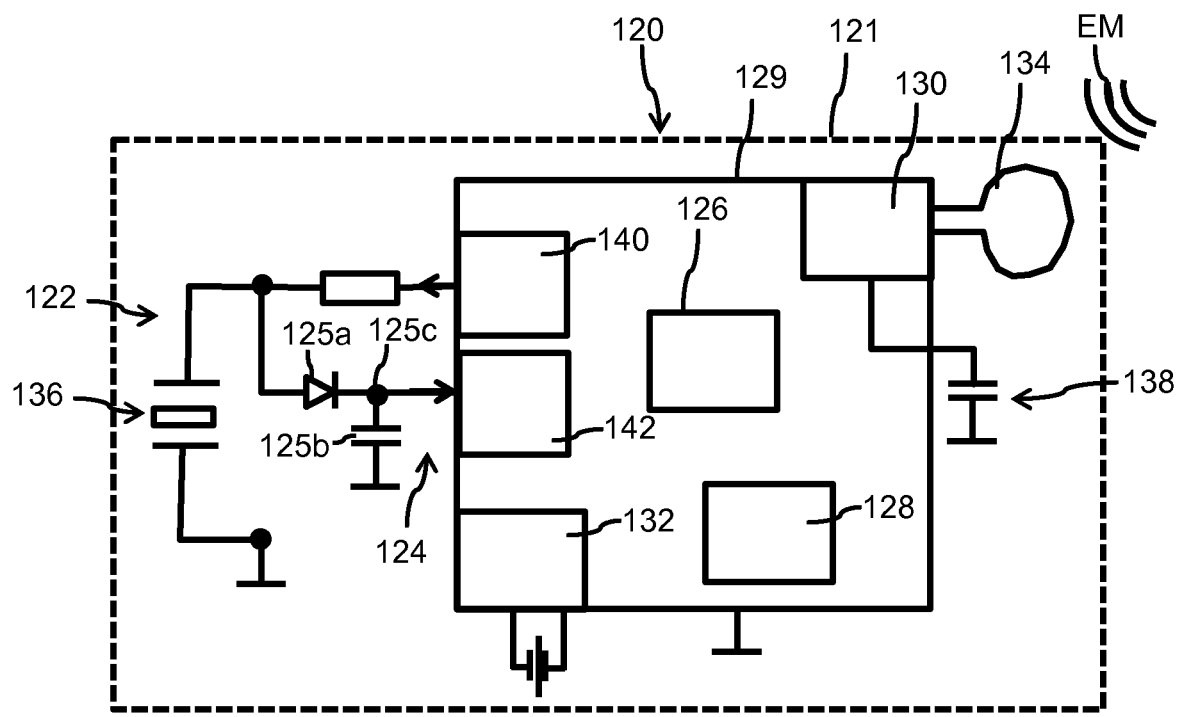
FIG. 4 is a block diagram of the measuring arrangement of FIG. 3.

The measuring arrangement 120 with its components is schematically illustrated in more detail in FIG. 4. The measuring arrangement 120 comprises a signal generator 122 that is configured to emit a measurement signal S1 into or through the interior volume 109. The measurement signal S1 can be an acoustic signal. The acoustic signal may comprise a mechanical excitation or a mechanical vibration.

The measuring arrangement 120 further comprises a signal detector 124 that is configured to detect a feedback signal F1. The feedback signal F1 is indicative of an interaction of the measurement signal with at least one of the sidewall 102, the outlet 116 and the interior volume 109. The feedback signal F1 can be one of an acoustic signal, an electromagnetic signal or an electric signal. By emitting the measurement signal S1 into the interior volume 109 a respective feedback signal F1 is generated that is directly indicative of the interaction of the measurement signal S1 with at least one of the sidewall 102, the outlet 116, the pierceable seal 106 or the interior volume 109. On the basis of the detected feedback signal F1 alone or on the basis of a comparison of the feedback signal F1 with the measurement signal S1 a precise determination of the size of the interior volume 109 can be provided. Based on the feedback signal F1 alone and/or based on the respective measurement signal S1 the longitudinal position of the bung 110 relative to the body 101 of the container 100 can be determined or measured. From this, a momentary size of the interior volume 109 can be derived.

The block diagram of FIG. 4 shows one example of a measuring arrangement 120. The measuring arrangement 120 may comprise a housing 121 that provides and enables an encapsulation of the measuring arrangement 120 in the inside of the body 111 of the bung 110. The measuring arrangement 120 comprises a processor 126. The processor 126 is a microprocessor, e.g. in form of a microcontroller or in form of an application-specific integrated circuit (ASIC). The measuring arrangement 120 may comprise a PCB 129. In the example of FIG. 4 the signal generator 122 of the measuring arrangement 120 comprises an electromechanical transducer 136. The transducer 136 is configured to transform an electrical signal into a mechanical vibration.

The transducer 136 and hence the signal generator 122 is configured to generate an acoustic signal and hence to generate and to emit an acoustic measurement signal S1 propagating into the interior volume 109 of the container 100. The signal generator 122 is driven by the processor 126. The transducer 136 may be connected to the processor 126 through a converter 140. The converter 140 may comprise a digital-to-analog (DAC) converter. The measuring arrangement 120 may further comprise a clock generator 132 as well as a data storage 128. The converter 140, the clock generator 132 and the data storage 128 might be individually connected to the processor 126. They may be integrated into the processor 126.

In one example the signal detector 124 comprises an electric impedance measurement circuit 125. The electric impedance measurement circuit 125 comprises at least one diode 125a and a capacitor 125b that are arranged parallel to the transducer 136. The diode 125a and the capacitor 125b are connected in series. A node 125c located between the diode 125a and the capacitor 125b is connected to a further converter 142. The further converter 142 is implemented as an analog-to-digital (ADC) converter. The converter 142 is also connected to the processor 126. By means of the electric impedance measurement circuit 125 the voltage across the signal generator 122 and hence across the transducer 136 can be measured and monitored. This provides an impedance measurement of the transducer 136.

When the signal generator 122, in particular the transit user 136 is driven at a frequency that matches with the momentary resonance frequency of the container 100 the Q factor of the signal generator 122 will be at a maximum. Since the impedance measurement circuit 125 and hence the node 125c connected to the converter 142 is connected in parallel to the signal generator 122 and hence to the transducer 136, there will arise a maximum voltage or a peak voltage at an input of the converter 142 as the frequency of the signal generator 122 matches or equals the resonance frequency of the container 100.

Typically, the transducer 136 is driven at variable frequency. The transducer 136 can be driven by the processor 126 and the converter 140 in a frequency sweep mode. Hence, the frequency at which the transducer 136 oscillates can be subject to well-defined and continuous variations, e.g. in accordance to the diagram of FIG. 5a. As indicated therein, the frequency v varies over time t. The transducer 136 can be driven with a monotonously increasing frequency or at a monotonously decreasing frequency. The transducer 136 can be repeatedly driven with such variable frequency profiles. For instance, the transducer 136 can be driven at variable frequencies that change in accordance to a saw tooth profile over time. Hence, the frequency of the transducer 136 may constantly and monotonously increase from a minimum frequency $v_{min}$ to a maximum frequency $v_{max}$ within a certain time interval δt. As soon as the maximum frequency $v_{max}$ has been reached the frequency signal v comes back to the minimum frequency $v_{min}$. In a subsequent time interval δd the frequency rises again to the maximum frequency $v_{max}$. Alternative to the illustration of FIG. 5a frequency may change in accordance to a different frequency profile, wherein the frequency constantly and monotonically decreases from a maximum frequency $v_{max}$ to a minimum frequency $v_{min}$ and abruptly returns to the maximum frequency.

The momentary frequency at each clock time is known to the processor 126.

Figure 5A:
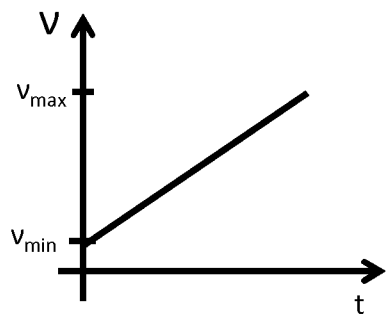
FIG. 5a is a diagram illustrating the frequency of an acoustic measurement signal over time.
Figure 5B:
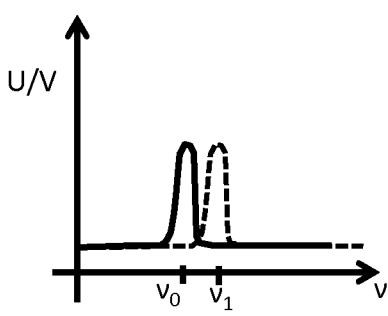
FIG. 5b is a diagram illustrating the resonance frequency of the container over time when subject to an acoustic excitation according to the diagram of FIG. 5a, FIG. 6 shows a flowchart of a method of determining the size of an interior volume of the container.

The frequency range between $v_{min}$ and $v_{max}$ is selected such that a resonance frequency or a higher harmonic of the resonance frequency of the container is larger than $v_{min}$ but smaller than $v_{max}$. In this way it is guaranteed, that at least one resonance frequency or a higher harmonic thereof is located between $v_{min}$ and $v_{max}$. During a variation of the frequency of the transducer 136 at a particular point of time the container 100 will be stimulated at a resonance frequency. If the momentary frequency of the transducer 136 matches the resonance frequency or a higher harmonic of the resonance frequency of the container 100 a well-defined peak can be measured by the electric impedance measurement circuit 125 as illustrated in FIG. 5b.

Here, for a certain frequency $v_0$ a well-defined and sharp peak evolves as the container 100 is acoustically stimulated by the transducer 136 at its momentary resonance frequency. As the injectable medicament 50 is expelled from the interior of the container 100 the total mass of the container 100 decreases. Accordingly, the resonance frequency will be subject to a detectable modification. For instance, the resonance frequency of the container may increase in response to a decrease of the total mass of the container 100. This shift of the resonance frequency, e.g. from $v_0$ to $v_1$ can be detected by the electric impedance measurement circuit.

From a substantial change of the detectable resonance frequency of the container the processor 126 can derive or calculate the size of the interior volume 109 and/or the longitudinal position of the bung 110. The processor 126 may be configured to determine and/or to detect a momentary resonance frequency of the container 100. The processor 126 may be further configured to determine or to calculate a modification between an initial resonance frequency $v_0$ to the momentary resonance frequency $v_1$. The difference of the resonance frequency $\delta v = v_1 - v_0$ is hence directly indicative of the volume change of the interior volume 109.

Upon manufacturing, assembly or filling of the container 100 with the injectable medicament 50 the resonance frequency of the container 100 can be individually determined. An initial resonance frequency $v_0$ may be stored in the data storage 128. Later on and during use of the container 100 and after a portion of the injectable medicament 50 has been expelled from the container 100, the momentary resonance frequency $v_1$ can be determined and its difference to the initial resonance frequency $v_0$ can be calculated. The difference in resonance frequency is a direct indication of the change of the size of the interior volume 109 and/or a direct indication of the longitudinal position of the bung 110 relative to the body 101 of the container 100.

When the signal detector 124 is implemented as an electric impedance measurement circuit 125 the signals obtained from the signal detector 124 are mapped to the signals emitted by the signal generator 122. Here, the processor 126 is connected to both, the signal generator 122 and the signal detector 124.

Moreover, the converters 140, 142 as well as the processor 126 are driven by the same clock signal. The processor 126 and the converters 140, 142 are synchronized on the basis of the clock signal provided by the clock generator 132. In this way the peak in the signal measured by the electric impedance measurement circuit 125 can be precisely mapped and assigned to a respective frequency in accordance to the graph as illustrated in FIG. 5a.

They may be provided further options and solutions to detect a resonance frequency of the container by means of a signal detector 124 integrated into a signal generator 122. One solution of a combined signal generation and signal detection may include a first oscillator and a second oscillator, wherein the second oscillator is driven or controlled by a reference. The first and the second oscillator are connected by way of a mixer and an output signal of the mixer is used as a DC signal thus being illustrative of the resonance frequency of a system or entity that is driven by the second oscillator.

In another example, the signal detector 124 may comprise a direct digital gate frequency measurement arrangement. Here, a preconditioned input signal is applied to one of the inputs of a digital AND gate. A second input to the gate is generated from a time base oscillator by the use of a configurable divider network. This provides a positive pulse of a required duration called the gate time ($T_{gate}$). While the pulse is in a high state the input signal passes through the AND gate and the number of its rising edges is counted by the counting register. Thus the number of cycles N of the input signal that fits within know predefined period of time $T_{gate}$ is obtained. The input signal frequency is then calculated as $F=N/T_{gate}$.

As an alternative or in addition to the electric impedance measurement circuit 125 the signal detector 124 may comprise an acoustic sensor 127. The acoustic sensor 127 may comprise a microphone. The acoustic sensor 127 may be also connected to the converter 142, hence to the analogue-to-digital converter 142. The acoustic sensor 127 is configured to measure at least one of a frequency and an amplitude of a feedback signal F1. If the signal generator 122 and hence the transducer 136 is driven in frequency sweep mode the acoustic sensor 127 will be configured to detect and to sense a frequency at which the amplitude of the respective feedback signal F1 is at a maximum or at a minimum. In this way a singularity or a peak of the acoustic response of the container can be directly determined.

The measuring arrangement 120 may further comprise a communication interface 130 that is configured to exchange data with an external electronic device 400 as illustrated in FIG. 2. The external electronic device 400 typically comprises a processor 402, a data storage 404 and a communication interface 406. The communication interface 406 is configured to communicate and to exchange data with the communication interface 130 of the measuring arrangement. Typically, the communication interface 130 as well as the communication interface 406 is or are configured for wireless data transmission. The communication interface 130 and/or the communication interface 406 might be configured to communicate via RF electromagnetic signals. The communication interfaces 130, 406 may be for instance configured for wireless communication in accordance to the Wi-Fi standard (IEEE802.11), RFID or NFC communication or Bluetooth communication protocols and standards.

The measuring arrangement 120 may further comprise an antenna 134 in order to enable wireless data transmission between the measuring arrangement 120 and an external electronic device 400. The antenna 134 may be further configured to withdraw electromagnetic energy from an external electromagnetic field EM, e.g. from a radio-frequency field (RF). It is generally conceivable, that the measuring arrangement 120 is entirely driven by electromagnetic energy withdrawn from an external electromagnetic field EM. Alternatively or additionally it is conceivable that the measuring arrangement 120 comprises an electric energy storage 138, e.g. implemented as a rechargeable battery. The electric energy storage 138 may be connected to the antenna 134 as well as to the processor 126. The electric energy storage 138 can be recharged by electric energy withdrawn from the external electromagnetic field EM through the antenna 134.

It is generally conceivable, that the processor 126 is limited to transfer electric signals obtainable from the converters 140, 142 via the communication interface 130 to the external electronic device 400. In this way, computational power of the measuring arrangement 120 as well as electric power consumption could be reduced to a minimum. The processing of signals of the converters 140, 142 may be entirely conducted by the processor 402 of the external electronic device 400. Hence, a software application implemented in the external electronic device 400 may provide a calculation of the size of the interior volume 109 and may be configured to determine the momentary filling level of the container 100.

With another example the processor 126 may be configured to determine or to calculate the size of the interior volume 109 based on the signals provided to the converter 140 and returned from the converter 142. Pre-processed signals or unprocessed signals of the detector 124 and/or processed data derived from a detected feedback signal and/or from an emitted measurement signal may be also stored in the data storage 128. Communication and transfer of data between the measuring arrangement 120 and the external electronic device 400 may be thus limited to the size of the interior volume and/or to the momentary longitudinal position of the bung 110 relative to the body 101 of the container 100.

Furthermore, it is conceivable, that the data storage 128 is configured to store numerous size information regarding the interior volume or regarding the longitudinal position of the bung 110. The data storage 128 may be configured to store a dosing history. The data storage 128 may be configured to store data derived from the measurement signal S1 and/or from the feedback signal F1 together with a timestamp. In this way a dosing history of the container 100 may be stored inside the bung 110.

Figure 6:
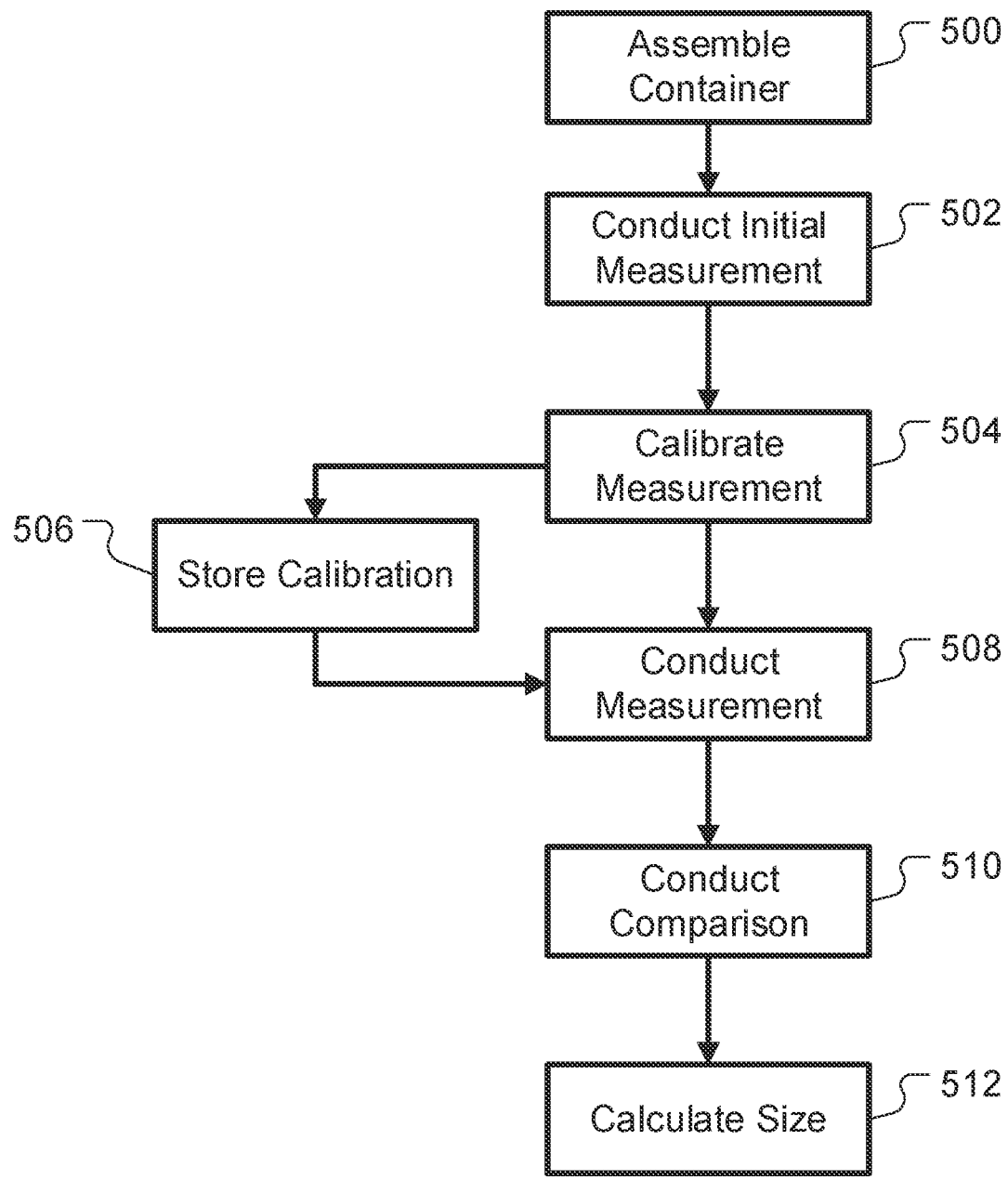

In the flowchart of FIG. 6 various method steps of the method of determining the size of the interior volume 109 are illustrated. In an initial step 500 the container 100 is assembled. Here, the bung 110 is inserted into the body 101 of the container 100. Thereafter the outlet 116 may be sealed, e.g. by arranging the pierceable seal 106 on the head portion 105a of the container 100. In a subsequent step 502 an initial measurement is conducted. Here, the signal generator 122 is triggered to emit at least one measurement signal S1 into or through the interior volume 109. At least one or a sequence of feedback signals F1 is or are detected by the signal detector 124. Thereafter in a subsequent step 504, the measured signals are calibrated. Hence, the results of the initial measurement are assigned with the actual size of the interior volume 109 that is determined or predetermined during the assembly process.

In step 506 a calibration is stored in the data storage 128. Later on and during use of the container, e.g. in an injection device the measuring arrangement 120 may be triggered to conduct a respective measurement and to emit at least a measurement signal S1 into or through the interior volume 109 in step 508. Accordingly, at least one or a series of feedback signals F1 is or are received by the signal detector 124. At least one of the measurement signals S1 and the feedback signals F1 is or are compared with the data stored in the data storage 128. This comparison is conducted in step 510. In the final step 512 there is derived or calculated the size of the interior volume 109 in on the basis of the comparison.

It should be noted, that various modifications to the flowchart as described above with respect to FIG. 6 are conceivable in accordance to the functionality of the various examples of the measuring arrangement and its interaction with, e.g. an external electronic device 400.

LIST OF REFERENCE NUMBERS 1 injection device
2 distal direction
3 proximal direction
11 piston rod
14 drive mechanism 16 dose dial
18 trigger
20 housing
21 cartridge holder
22 body
23 through opening
24 cap
25 window
26 window
27 inner needle cap
28 outer needle cap
31 socket
32 thread
40 injection needle
41 needle hub
50 medicament
100 container
101 body
102 sidewall
103 distal end
104 proximal end
105 neck portion
105a head portion
106 pierceable seal
107 shoulder portion
108 ferrule
109 interior volume
110 bung
111 body
113 distal face
114 proximal face
115 sidewall
116 outlet
120 measuring arrangement
121 housing
122 signal generator
124 signal detector
125 impedance measurement circuit
126 processor
127 acoustic sensor
128 data storage
129 printed circuit board
130 communication interface
132 clock generator
134 antenna
136 transducer
138 electric energy storage
140 converter
142 converter

The invention claimed is:

1. A container for an injectable medicament, the container comprising:
an elongated body having a tubular-shaped sidewall extending along a longitudinal axis and having a distal end and a proximal end,
an outlet at the distal end,
a bung arranged inside the elongated body, sealingly engaged with the tubular-shaped sidewall and slidable along the longitudinal axis relative to the tubular-shaped sidewall,
an interior volume to receive the injectable medicament and being confined by the tubular-shaped sidewall, by the outlet, and by the bung, and
a measuring arrangement arranged in or on the bung, the measuring arrangement comprising:
a signal generator configured to emit (i) a first measurement signal into or through the interior volume and (ii) a second measurement signal into or through the interior volume, the first measurement signal being capable to stimulate or to excite a first resonance frequency of the container and the second measurement signal being capable to stimulate or to excite a second resonance frequency of the container, the second resonance frequency being greater than the first resonance frequency, and
a signal detector configured to detect (i) a first feedback signal indicative of a first resonating interaction of the first measurement signal with the container and (ii) a second feedback signal indicative of a second resonating interaction of the second measurement signal with the container,
wherein the first resonance frequency represents a fundamental resonance frequency of the container such that the first feedback signal indicative of the first resonating interaction represents a fundamental resonance of the container, and
wherein the second resonance frequency represents a harmonic resonance frequency of the container such that the second feedback signal indicative of the second resonating interaction represents a harmonic resonance of the container.

2. The container according to claim 1, further comprising a processor connected to the signal detector, the processor configured to determine a size of the interior volume based on the first resonating interaction and the second resonating interaction.

3. The container according to claim 2, wherein the processor is connected to the signal generator, wherein the processor is configured to:
trigger the emission of the first measurement signal and the second measurement signal, and
determine the size of the interior volume based on a comparison of the first measurement signal with the first feedback signal and a comparison of the second measurement signal with the second feedback signal.

4. The container according to claim 1, wherein the measuring arrangement comprises a data storage configured to store at least one of an initial size of the interior volume, the first feedback signal, or the second feedback signal.

5. The container according to claim 1, further comprising:
a communication interface configured to exchange data with an external electronic device,
an antenna configured to withdraw electric energy from a surrounding electromagnetic field, and
an electric energy storage connected to the antenna and configured to store the withdrawn electric energy from the surrounding electromagnetic field.

6. The container according to claim 1, wherein the signal generator is an acoustic signal generator configured to emit acoustic measurement signals of a variable frequency.

7. The container according to claim 6, wherein the signal generator is configured to generate and to emit a series of measurement signals of increasing frequency or decreasing frequency.

8. The container according to claim 6, wherein the signal generator comprises an electromechanical transducer configured to generate and to emit measurement signals in an ultrasound frequency range.

9. The container according to claim 1, wherein the signal detector comprises an electric impedance measurement circuit connected to the signal generator.

10. The container according to claim 1, wherein the signal detector is integrated into the signal generator or the signal detector is a component of the signal generator, and the signal detector comprises an acoustic sensor comprising a transducer configured to convert acoustic signals into electric signals.

11. The container according to claim 1, wherein the first resonating interaction of the first measurement signal with the container represents a fundamental resonance of at least one of the tubular-shaped sidewall, the outlet, the bung, or the interior volume.

12. The container according to claim 11, wherein the second resonating interaction of the second measurement signal with the container represents a harmonic resonance of the at least one of the tubular-shaped sidewall, the outlet, the bung, or the interior volume.

13. The container according to claim 12, wherein the at least one of the tubular-shaped sidewall, the outlet, the bung, or the interior volume is at least one of the tubular-shaped sidewall, the outlet, or the bung.

14. The container according to claim 13, wherein the at least one of the tubular-shaped sidewall, the outlet, or the bung is the bung, and the measuring arrangement is arranged in the bung.

15. The container of claim 1, wherein the container comprises a pierceable septum located at the outlet of the container, the first resonating interaction of the first measurement signal with the container represents a fundamental resonance of the outlet of the container, and the second resonating interaction of the second measurement signal with the container represents a harmonic resonance of the outlet of the container.

16. A method of determining a size of an interior volume of a container for an injectable medicament, the container comprising an elongated body having a tubular-shaped sidewall extending along a longitudinal axis and having a distal end and a proximal end, an outlet at the distal end, a bung arranged inside the elongated body, sealingly engaged with the tubular-shaped sidewall and slidable along the longitudinal axis relative to the tubular-shaped sidewall, the interior volume to receive the injectable medicament and being confined by the tubular-shaped sidewall, by the outlet and by the bung, and a measuring arrangement arranged in or on the bung, the method comprising:
generating and emitting (i) a first measurement signal from the measuring arrangement into or through the interior volume of the container and (ii) a second measurement signal into or through the interior volume, wherein the first measurement signal is capable to stimulate or to excite a first resonance frequency of the container and the second measurement signal being capable to stimulate or to excite a second resonance frequency of the container,
detecting (i) a first feedback signal indicative of a first resonating interaction of the first measurement signal with the container and (ii) a second feedback signal indicative of a second resonating interaction of the second measurement signal with the container, and
determining the size of the interior volume based on the first feedback signal and the second feedback signal,
wherein the first resonance frequency represents a fundamental resonance frequency of the container such that the first feedback signal indicative of the first resonating interaction represents a fundamental resonance of the container, and
wherein the second resonance frequency represents a harmonic resonance frequency of the container such that the second feedback signal indicative of the second resonating interaction represents a harmonic resonance of the container.

17. The method of claim 16, further comprising:
triggering the emission of the first measurement signal and the second measurement signal, and
determining the size of the interior volume based on a comparison of the first measurement signal with the first feedback signal and a comparison of the second measurement signal with the second feedback signal,
wherein the second resonance frequency is greater than the first resonance frequency.

18. The method of claim 16, wherein determining the size of the interior volume based on the first feedback signal and the second feedback signal comprises determining at least one of a magnitude or an amplitude of the first feedback signal and the second feedback signal.

19. The method of claim 16, wherein determining the size of the interior volume based on the first feedback signal and the second feedback signal comprises determining a time or time delay at which the first feedback signal or the second feedback signal is detected.

20. The method of claim 16, wherein determining the size of the interior volume based on the first feedback signal and the second feedback signal comprises monitoring and processing a temporal variation of the first feedback signal or the second feedback signal.

21. A container for an injectable medicament, the container comprising:
an elongated body having a tubular-shaped sidewall extending along a longitudinal axis and having a distal end and a proximal end,
an outlet at the distal end,
a bung arranged inside the elongated body, sealingly engaged with the tubular-shaped sidewall and slidable along the longitudinal axis relative to the tubular-shaped sidewall,
an interior volume to receive the injectable medicament and being confined by the tubular-shaped sidewall, by the outlet, and by the bung, and
a measuring arrangement arranged in or on the bung, the measuring arrangement comprising:
a signal generator configured to emit (i) a first measurement signal into or through the interior volume and (ii) a second measurement signal into or through the interior volume, the first measurement signal being capable to stimulate or to excite a first resonance frequency of the container and the second measurement signal being capable to stimulate or to excite a second resonance frequency of the container, the second resonance frequency being greater than the first resonance frequency, and
a signal detector configured to detect (i) a first feedback signal indicative of a first resonating interaction of the first measurement signal with the container and (ii) a second feedback signal indicative of a second resonating interaction of the second measurement signal with the container,
wherein the first resonating interaction of the first measurement signal with the container represents a fundamental resonance of at least one of the tubular-shaped sidewall, the outlet, the bung, or the interior volume; and
wherein the second resonating interaction of the second measurement signal with the container represents a harmonic resonance of the at least one of the tubular-shaped sidewall, the outlet, the bung, or the interior volume.

22. The container according to claim 21, wherein the at least one of the tubular-shaped sidewall, the outlet, the bung, or the interior volume is at least one of the tubular-shaped sidewall, the outlet, or the bung.

* * * * *